United States Patent [19]

Hardy et al.

[11] 4,038,976
[45] Aug. 2, 1977

[54] PULSE INDICATOR

[76] Inventors: Frank M. Hardy, 1322 Dauphine St., Silver Spring, Md. 20906; Theodore W. Coffey, 806 College Parkway, Rockville, Md. 20850

[21] Appl. No.: 558,366
[22] Filed: Mar. 14, 1975
[51] Int. Cl.² .............................................. A61B 5/02
[52] U.S. Cl. ........................... 128/2.05 P; 128/2.05 T
[58] Field of Search .................... 128/2.05 E, 2.05 P, 128/2.05 R, 2.05 T, 2.06 F, 2.06 R

[56] References Cited

U.S. PATENT DOCUMENTS

| | | | |
|---|---|---|---|
| 2,769,929 | 11/1956 | Hardway, Jr. | 128/2.05 P |
| 2,918,054 | 12/1959 | Goolkasian | 128/2.05 T |
| 3,426,747 | 2/1969 | Herman et al. | 128/2.05 P |
| 3,556,084 | 1/1971 | Budde | 128/2.05 P |
| 3,838,684 | 10/1974 | Manuel et al. | 128/2.05 P |

Primary Examiner—William E. Kamm

[57] ABSTRACT

A portable electrical device having both flashing light and/or sound transmitting means activated by a transducer so that the transducer or the entire assembly may be mounted in pressure sensitive contact with a pulsing area of a living body to convert pulses to visible light flashes or sound beats adjustable in pressure sensitive pickup to reflect and monitor the blood flow through the pulse.

17 Claims, 7 Drawing Figures

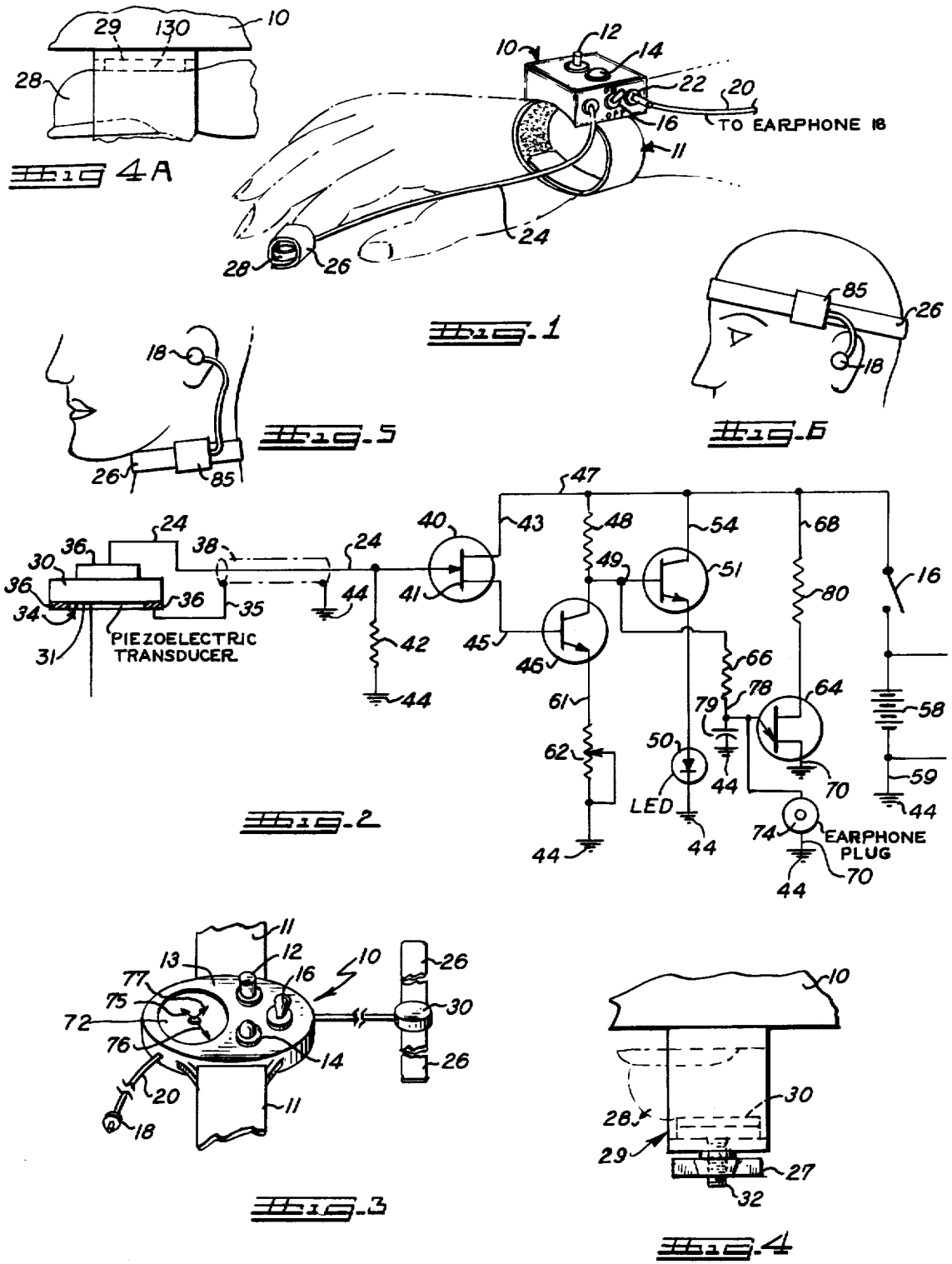

PULSE INDICATOR

This invention relates to portable signaling means for monitoring a pulse in a living body including an element for contact of a pulsing area and reflecting a pulse signal, indicating the condition, such as the regularity of blood coursing through the sensing point of the pulse; and thus indicating the blood flow condition at that point, for both visual as well as audible perception. More particularly, the device is portably mounted to a warm blooded animal, such as a human body, where the sensing element is mounted via a pressure responsive contact with a pulsing area, and an electrical circuit means is provided to convert the pressure responsive pulse signal either visibly or audibly or both to receive and read the pulsing effect.

The device hereof is intended for both public and professional use to be a small portable means for being easily carried, usually by a human such as upon his wrist or other convenient pulse detection point and for displaying, assessing, or evaluating the pulse pressure from that point. The device may be fastened such as by strapping around his wrist. The device has a pulse pressure responsive element to be mounted in pressure responsive position upon the pulse area which transfers the pulsing pressure as an electrical signal to an electrical means. The pressure induced signal of the pulse, and circuit means carried by the device, generally activated by battery means, converts the pulse signal either to a visible light varying in output with the pulsing signal or alternately to an audible signal or both in combination. The visible and audible signals can be adjusted to separate the pulse pressure into a single beat, visible or audible, to assess the pulse rate, or it can be adjusted to display the pulse in its several pressure varied phases, as a function of the actual pulsing blood characteristic through the selected pulsing artery from which the pulse is monitored. Similarly, the sound output, where the signal is converted audibly, will be sound beats.

Thus, the present device may be adjusted sufficiently sensitive to pick up such pulse signals. In the case of the visible signal light output, it may be a series of single flashes synchronous with and responsive to the pulse as beats; or it can be adjusted to visibly reflect the pulse in its several pressure varied phases of the pulse. Similarly, in the case of the audible output, the sound may represent a series of single beats of the pulse, or the specific sounds of its rhythic or arrhythonic cycles as the case may be, heard audibly. Thus, the pulse can be monitored visibly and audibly by the wearer, or by his physician or nurse merely by observing the output signals of the wearer. The audible signal, similarly, can have its audible output rendered loud enough for audible pickup by anyone listening in the vicinity, or it may be a small enough audible output to be picked up only by an earphone worn by the listener.

The device is intended, therefore, both as a pulse monitoring device that can be used by a physician or nurse, evaluating the pulse condition of a patient, who may be at rest or going through various physical exercises; or it may be used by the wearer himself who may use the portable device carrying it with him in normal movement to observe the effect of the amount of exercise he is doing. It may be used by a wearer merely to monitor his own pulse rhythm at times of worry, stress or suspicion that his heart is not functioning properly. It may be used by a person having a heart condition to determine his exercise threshold to accommodate for his capacity. It may be used by a patient in a hospital or nursing home to signal his condition continuously and visibly so that a passing nurse or physician can observe it. It may also be used by an emergency squad visiting a stricken person, or when conveying a heart stricken patient in an ambulance, and applied at the site of a heart attack to determine an approximate pulse rate and strength or condition. Finally, it may be used for analysis of arrythmias under psychological stress and by persons exercising at great depths, or other stress conditions such as divers, astronauts, test pilots, and others operating under unusual heart stress conditions. Thus, the device will have substantially wide use both professionally and by individuals.

In a typical aspect, the invention comprises circuitry to amplify a pulse pressure signal mounted in a small portable housing, together with power means such as a small battery for activating the circuit and a pressure sensitive pickup means usually including a transducer mountable in contact with the pulse and connected to feed the electrical output to the pressure responsive circuit. The circuit means will contact a visible output such as, typically, a light emitting diode to render the pulse generated current output visible. That output may alternately, or in combination, be passed to audible means, whereby the sound generated by the same pulse induced signal is made audible.

The invention is further described in a specific embodiment in the drawings in which:

FIG. 1 illustrates, in diagrammatic form, a physical structure in which the circuit may be mounted about the wrist of the user;

FIG. 2 is an electrical diagram illustrating the circuitry including a pressure sensitive transducer of FIG. 1;

FIG. 3 shows a portion of the assembly of FIG. 1 mountable as a wrist watch;

FIG. 4 is a detail showing the fastening of the transducer to the pulse on a finger;

FIG. 4A shows an alternate arrangement having the transducer carried by the housing;

FIG. 5 illustrates the fastening of the transducer to the pulse responsive area of the temple and FIG. 6 shows the fastening and the transducer to the pulse responsive area of the neck.

As shown in FIG. 1, a housing 10 is provided for enclosing the several electrical elements and circuitry. This housing is shown in FIG. 1 as rectangular, but it may be in the form of a fine electrical instrument such as a wrist watch and may even include the normal time measuring elements usual in a watch or time piece in addition to the circuitry and control elements hereof as shown in FIG. 3.

For control, the housing 10 shown in FIG. 3 encloses the wiring elements shown in FIG. 2, as will appear, a sensitivity adjustment knob 12 protrudes from one exposed surface 13. A visibly mounted indicator light 14 shows by pulsing light flashes the pulse condition being sensed. An off-on electrical switch 16 is exposed for manual operation connected with the internal circuitry. An earphone 18 connected by wire 20, may be plugged by a jack-type connector 22 into the circuit whereby the pulse may be made audible.

In alternate construction not shown, the audible output may be a radio of any type, such as FM signaling type, and the earphone may be an FM receiver whereby the output of the signal may be broadcast and received in the receiver of the user, whether his own pulse is being monitored or others, receiving the sound through the ear piece such as a physician within the broadcast area, who may pick up the signal from an ear piece, audibly. Other readily portable forms of modulating and amplifying the signal both visibly and audibly can be substituted. It also shows methods of attachment to the body in specific areas can be substituted depending upon the wearers activity such as head or collar band as shown in FIGS. 5 and 6, respectively. The transducer and the electrical circuit means in the case of FIGS. 5 and 6 are mounted in the same housing 85 with the audible signal output being conveyed to the wearer by earphone 18.

The circuit as shown in FIG. 2 contacts with the pulse by way of a pickup sensor which may be a transducer crystal 30 mounted in pressure transfer contact with the pulse with its output passed to the circuit line 24. The transducer crystal 30 is held by a binding or supporting strap 26 mounted to a pulse to be monitored such as a finger tip 28 or thumb of the person whose pulse is to be monitored. As shown in FIG. 1, the strap 26 is wound and fastened about a finger 28 in pressure transferring contact with the pulse therein, and under close enough contact provided by the strap to transfer the pressure from the pulse in the finger to the transducer crystal which in turn converts the pressure to an electrical signal passing to the circuit of FIG. 2 by way of line 24.

In other practical structures, the transducer may be mounted in any useful support, such as a ring 29 which will be shaped or sized to be inserted over the pulse carrying member of the body such as a finger tip and a transducer itself can be adjustably mounted within the ring by the adjustment screw as shown in FIG. 4 whereby the pressure of the transducer 30 against the pulse of the finger tip 28 may be manually adjusted to a sensitively set pressure for optimum transfer of the pressure of the pulse to the transducer. As shown in the detail of FIG. 4, the body member 28 has the transducer crystal 30 supported from a ring or housing 29 and the adjustment screw 32 and nut 27 thereon adjustably presses the transducer 30 into optimum pulse pressure transferring contact with the finger. The transducer may also be an integral part of the device thereby eliminating the need for interconnecting the transducer with the housing.

As shown in FIG. 2, the contact with the pulse is made upon a surface 31 of the crystal 30, pressing it against the pulse as bearing in the direction of the arrow 34 upon its surface. The crystal 30 is surrounded by pickup plates 36 through which the pressure induced circuit in the crystal generates a voltage in line 24 generally protected by a shield 38 having one end connected to contact the face 31 of the transducer crystal 30 and other end is grounded at 44.

The voltage in line 24 is passed to the gate 41 of a field effect transistor 40 having a drain 43 and a source 45 provided with a bias return resistor 42 and thence to a ground 44. The output of the field effect transistor 40 is connected to the base of transistor 46 and to the positive terminal of battery 58 through switch 16 by way of line 47. Transistor 46 is connected through a load resistor 48 and thence to a pole of battery 58 through switch 16. The output of the transistor 46 drives an emitter follower amplifier transistor 51 by way of line 49, the output of which drives the light emitting diode 50 responsive to the pickup in crystal 30. The circuit is completed therefrom to the ground 44 from the cathode of the light emitting diode. The other leg of the emitter follower 51 through line 54 passes to the line 47 and off-on switch 16 and to the battery 58 whose negative terminal is grounded at 44 by way of line 59. The circuit includes a leg 61 which for sensitivity adjustment, comprises a variable resistor 62 for adjusting the bias of transistor 46. That adjustment will allow variation of the light output in the diode 50 developed from the pressure signal passed from the crystal 30 in line 24 to be adjusted variably from a single pulse flash to a more sensitive flash, indicative of the various pressure elements of a pulse beat, to show this visibly. Indeed the several elements of a pulse beat can be seen and read by an experienced eye as to brightness or rhythm.

For purposes of making the circuit audible, the pulse signal is coupled to a second stage 64 through resistor 66 taking its power supply current from line 68 and resistor 80 and grounding through line 70. An earphone plug 74 connected to line 78 is provided to pick up the signal output of the unifunction transistor 64 audibly in direct tone coincidence with the light flashes of the diode 50, sensitized either as single tone or varied tone by sensitivity adjuster 62 to indicate the condition audibly of the pulse. In this manner by varying the sensitivity of the adjustment 62 both the visible light output of diode 50, as well as the sound picked up by an earphone attached through earphone plug 74, will be sensitized to a degree needed or desired. Resistors 48 and 66 and capacitor 79 comprise the timing circuit for the tone generation. That tone output is coincident with the pulse signal and is turned off when the pulse signal is not present. The sensitivity adjustment 62 is connected to knob 12, the positioning of the resistor and adjustment is then made by twisting of knob 12.

The housing 10 in both FIGS. 1 and 3 are shown supported about the wrist of a user by a strap 11 and a separate fastening of the transducer 30 in pressure responsive contact with a finger tip 28 is provided by a strap 26. FIG. 4 shows the pressure upon the finger tip engaging the transducer 30 is adjusted by the screw 32 and nut 27 reacting against the housing 29, thus to press the transducer into adjusted pressure transferring contact with the pulse in the finger tip. However, in alternate position, as shown in FIG. 4A, the transducer 130 transducer itself may be mounted extending and supported from part of the housing wall 10 and the ring 29 is mounted integral with the housing wall. In that position the finger tip is pressed against the transducer plate 130 at the housing wall. In that construction the pressure transferring contact as well as the circuitry are both carried by the housing 10 with the transducer mounted in or upon the wall thereof in exposed pressure transfer position. In that manner both the housing and pressure transferring transducer are a single integrally constructed unit. Moreover, as shown in FIG. 5, the entire housing unit 85 with the transducer crystal exposed on its inner wall can be strapped about the temple to contact an artery therein; or as shown in FIG. 6 that unit 85 may be strapped against the throat for contact of an artery, and thus measure the pulse as desired from these, or analogously other places.

Certain other modifications will occur to those skilled in the art. As shown in FIG. 3, the circuit may be housed in a smaller round housing and strapped about the wrist for easy portability, and that housing may also carry the operating elements of a time piece, a wrist watch, and show the time in hours, minutes and seconds by hands 75, 76 and 77, through glass or light transmissive wall 72 respectively so that the time of the flashes or sound can be measured as well. Applicant, prefers for the light source a light emitting diode 50 as shown, but less desirably a light bulb, since the light output of such bulb is not visibly so sensitive or efficient to visibly indicate the pulse condition as the diode. The strap means 11 or 26 as shown has velcro fastener for quick fastening and unfastening at a comfortable as well as pulse transferring pressure for variably sized body members such as a wrist, ankle or the like, but the fastening means can be placed on any other comfortably applied portion of the body for portably carrying the entire assembly; and the pressure sensitive crystal input means too may be sized, shaped and supported in a manner for quick fastening upon any pulsing source, variable from the heart area itself to any portion of the body including a limb, throat, head, or the like.

In use, referring to FIG. 1, the user will ordinarily fasten the housing 10 through the wrist strap on a person's wrist and then fasten the pressure sensitive transducer to the pulse area to be monitored by strap 26, to monitor the pulse condition. He can go through certain exercises. He thus may increase the pulse and vary the conditions, a great convenience for testing an exercising patient by a doctor or nurse. It may be used similarly by a person exercising such as jogging or other forms of exercise using the light pulses or sound pulses as indicators to signal when his exercise is at a sufficiently strenous pace. It may be used similarly, perhaps continuously, by a heart patient to alert him when his pulse is irregular and his condition is in a critical or is changing from a critical phase. The heart patient may be use of the audible signal output of the device transmit the sound pulses via a telephone or other long distance communication system to his doctor, who in turn may advise the patient of emergency procedures to follow. Other manners of use and uses for measurement of a pulse condition will occur to those skilled in the art. Accordingly, it is intended that the description and drawings given herein be regarded as exemplary and interpreted as defined in the claims appended hereto.

We claim:

1. A portable pulse signaling device comprising a portable pressure sensor comprising a transducer and means for supporting said transducer in pressure sensitive contact with a body pulse area, means for discriminately adjusting the pressure of said transducer upon said pulse area whereby the periodic pulsing pressure therein upon said transducer is coverted into electrical signals significant of component pressure variations in said pulse, a portable amplifier electrical circuit means connected to and responsive to said pressure adjusted transducer to produce amplified electrical pulses, and a light emitter in said circuit responsive to the adjusted pressure visibly indicating said pulses by corresponding light flashes.

2. Portable pulse signaling device as defined in claim 1 including a housing, said amplifier electrical circuit means being disposed in said housing, means for portably supporting said housing by the body being tested, said light emitting means being visibly exposed in a wall of said housing and means in said circuit for adjusting its sensitivity to the pressure variations in the pulses visibly indicating by variations of said light the actual pulsing pressure variations of the blood flow from the heart through said pulse.

3. The device as defined in claim 1 including a housing means for fastening said housing to a body member, a light transmissive wall, a clock work mechanism including hands indicating the time as a time piece disposed in said housing with the light transmissive hands visibly exposed through said wall for reading the time, said housing further enclosing said portable amplifier electrical circuit means with said light means visibly exposed in a wall of said housing, and off-on switch means in a wall of said housing for manual control of said electrical circuit.

4. The device as defined in claim 1 including a housing, means for fastening said housing to a body member, said transducer being mounted in a wall of said housing with a surface exposed whereby both said housing and transducer as an integral assembly may be mounted by said support means in pressure sensitive contact with a body pulse.

5. The device as defined in claim 4 wherein the housing is further combined with a sound signaling device emitting sound signals in pulses responsive to the pulsed electrical signal induced by said transducer.

6. The device as defined in claim 4 wherein the support for said housing and transducer in pressure transmitting contact is integrally mounted with the housing and a rigid ring in which a finger may be inserted for contact with the transducer in a wall thereof is fastened to and supported by said housing.

7. The device as defined in claim 6 wherein the housing is further combined with a sound signaling device emitting sound signals in pulses responsive to the pulsed electrical signal induced by said transducer.

8. The device as defined in claim 1 including means for fine adjusting of said circuit to reflect the pressure pulses picked up by said transducer in sufficient sensitivity to separate the pressure into its minor variations, corresponding to the actual pulsing pressures directly reflecting output of the blood flow from the heart through said pulse.

9. A portable pulse signaling device comprising a portable pressure sensor comprising a transducer and means for supporting said transducer in pressure sensitive contact with a body pulse area, means for discriminately adjusting the pressure of said transducer upon said pulse area whereby the periodic pressure therein is converted by said transducer into electrical signals significant of component pressure variations in said pulse, a portable amplifier electrical circuit means connected to and responsive to said pressure adjusted transducer to produce amplified electrical pulses, and a sound generating device emitting sound signals in pulses responsive to the adjusted pressure signals on said transducer audibly indicating said pulses by corresponding sound signals.

10. Portable pulse signaling device as defined in claim 9 including a housing, said amplifier electrical circuit means being disposed in said housing, means for portably supporting said housing by the body being tested, said amplifier electrical circuit means having means in a wall of said housing for connecting said circuit to said sound generating means, and means in said circuit for adjusting its sensitivity to the pressure of the pulse, audibly indicated by variations of emitted sound signals of said sound generating means, responsive pressure to the actual pulsing pressure variations of the blood flow from the heart through said pulse.

11. The device as defined in claim 9 including a housing, means for fastening said housing to a body member, a light transmissive wall, a clock work mechanism including hands visibly exposed through said wall for reading the time, said housing further enclosing said portable amplifier electrical circuit means, said amplifier electrical circuit means including means for connecting to said sound generating means, and off-on switch means in a wall of said housing for manual control of said electrical circuit.

12. The device as defined in claim 9 including means for fine adjusting of said circuit to reflect the pressure pulses picked up by said transducer in sufficient sensitivity to separate the pressure into its minor variations, corresponding to the actual pulsing pressures directly reflecting output of the blood flow from the heart through said pulse.

13. A portable pulse signaling device comprising a portable pressure sensor comprising a transducer and means for supporting said transducer in pressure sensitive contact with a body pulse area, means for discriminately adjusting the pressure of said transducer upon said area whereby the periodic pulsing pressure therein is converted by said transducer into electrical signals significant of component pressure variations in said pulse, a portable amplifier electrical circuit means, connected to and responsive to said pressure adjusted transducer to produce amplified electrical pulses and light and sound emitting means responsive to the pulses generated in said circuit to emit corresponding pulses of both light and sound responsive to adjusted pressure.

14. The portable pulse signaling device as defined in claim 13 including a housing, said amplifier electrical circuit means being disposed in said housing, means for portably supporting said housing by the body being tested, said light emitting means being visibly exposed in a wall of said housing, said amplifier electrical circuit means having means in a wall of said housing for connecting to said sound generating means, and means in said circuit for adjusting its sensitivity to the pressure of the pulse visibly an audibly indicated by variations of said light emitting and sound generating means responsive to the actual pulsing pressure variations of the blood flow from the heart through said pulse.

15. A portable pulse signaling device comprising a portable pressure sensor comprising a transducer and means for supporting said transducer in pressure sensitive contact with a body pulse whereby the periodic pulsing pressure thereof upon said transducer is converted into electrical signals, a portable amplifier electrical circuit means connected to and responsive to said transducer to produce amplified electrical pulses, a light emitter in said circuit visibly indicating said pulses by corresponding light flashes, said circuit further including means for fine adjusting of said circuit to reflect the pressure pulses picked up by said transducer in sufficient sensitivity to separate the pressure into its minor variations, corresponding to the actual pulsing pressures directly reflecting output of the blood flow from the heart through said pulse.

16. A portable pulse signaling device comprising a portable pressure sensor comprising a transducer and means for supporting said transducer in pressure sensitive contact with a body pulse area whereby the periodic pulsing pressure upon said transducer is converted to corresponding periodic electrical signals, a portable electrical amplifier circuit means connected to receive and amplify said electrical signals, said amplifying circuit including means for fine adjustment to reflect the pressure pulses in sufficient sensitivity to separate each pressure pulse into its minor variations, directly reflecting the sensed output pressures of the blood flow from the heart in the pulsed area, and means for sensibly signaling said minor pressure variations.

17. A portable pulse signaling device comprising a portable pressure sensor including a transducer and means for supporting said transducer in pressure sensitive contact with a body pulse area, a housing, a portable electrical amplifier in circuit means in said housing connecting to and responsive to said transducer-induced circuit to produce amplified electrical signals corresponding to said periodic pulsing pressure upon said transducer, a timing mechanism in said housing, mean exposed through a wall of said housing for visibly signaling both the output of said timing mechanism and pulsed output of said circuit, whereby to indicate a timed pulse rate.

* * * * *